United States Patent [19]

Peyman et al.

[11] Patent Number: 4,646,720
[45] Date of Patent: Mar. 3, 1987

[54] OPTICAL ASSEMBLY PERMANENTLY ATTACHED TO THE CORNEA

[76] Inventors: Gholam A. Peyman, 535 N. Michigan Ave., Chicago, Ill. 60611; Jeffrey E. Koziol, 601 W. Central, Mount Prospect, Ill. 60056

[21] Appl. No.: 711,005

[22] Filed: Mar. 12, 1985

[51] Int. Cl.[4] .......................... A61B 19/00; A61F 2/14
[52] U.S. Cl. ...................................... 128/1 R; 623/5; 128/303 R
[58] Field of Search ........................ 623/4-6; 128/1 R, 303 R; 604/893, 895

[56] References Cited

U.S. PATENT DOCUMENTS

| | | | |
|---|---|---|---|
| 2,714,721 | 8/1955 | Stone, Jr. .................................. | 623/5 |
| 4,466,705 | 8/1984 | Michelson ........................ | 604/895 X |
| 4,540,417 | 9/1985 | Poler .................................... | 604/895 |

FOREIGN PATENT DOCUMENTS 388746  10/1973  U.S.S.R. .................................. 623/5

OTHER PUBLICATIONS

Henry M. Clayman, Kerato—Refractive Symposium, 1983, pp. 19-21.

Primary Examiner—Ronald L. Frinks
Attorney, Agent, or Firm—Roylance, Abrams, Berdo & Goodman

[57] ABSTRACT

A device and method for permanently correcting refractive errors in the eye. An optical element, such as a lens, having at least one opening therein for the diffusion of nutrients from a recipient's cornea, is positioned on the recipient's cornea and held in place by an optical covering, such as a donor cornea. The covering covers the optical element, and is attached to the recipient's cornea by means of, for example, sutures.

19 Claims, 13 Drawing Figures

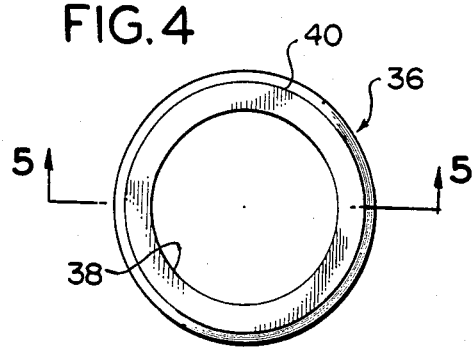
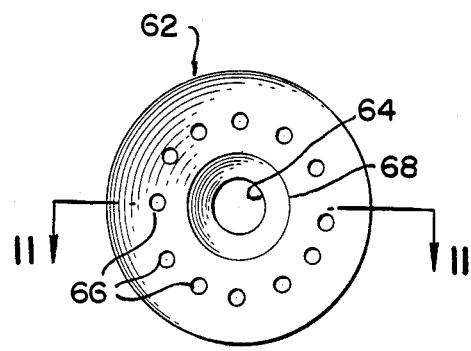
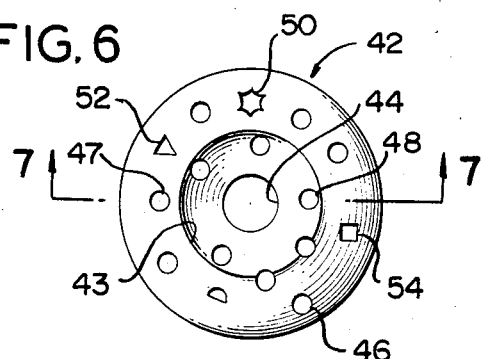
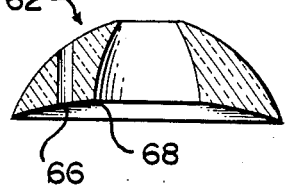
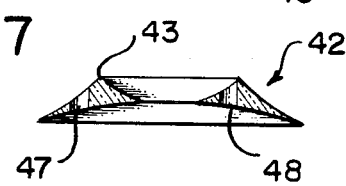
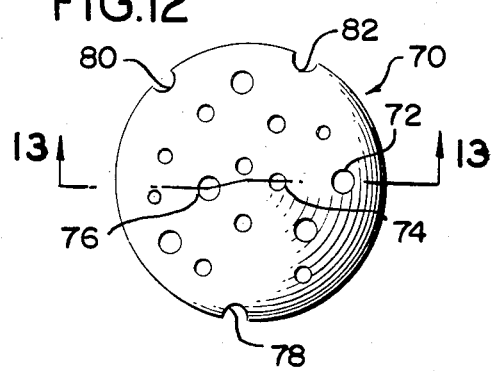
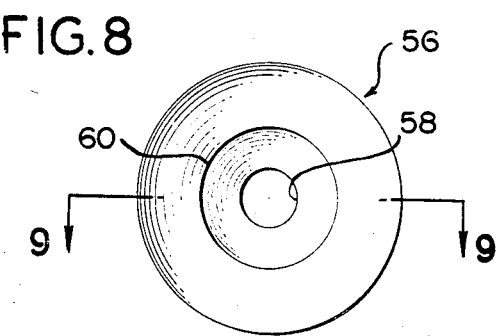
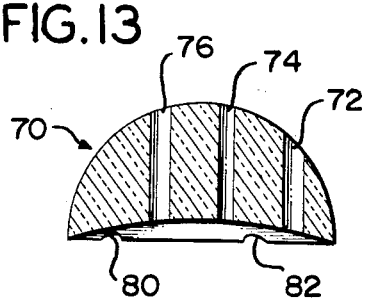
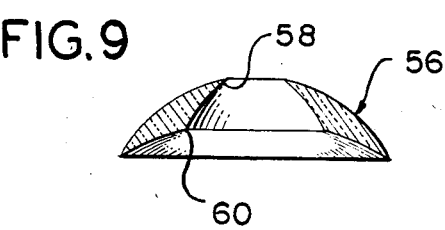

OPTICAL ASSEMBLY PERMANENTLY ATTACHED TO THE CORNEA

FIELD OF THE INVENTION

This invention relates to optical elements to be placed onto a patient's cornea to correct refractive errors of the eye. The element is held in place by an optical covering which is surgically attached to the patient's cornea.

BACKGROUND OF THE INVENTION

Refractive errors of the eye such as myopia, hyperopia, and astigmatism are among the most commonly experienced eye problems. The corrective measures for these problems have been either glasses or contact lenses. In recent years, however, numerous attempts at surgical correction of refractive errors have been attempted.

One such technique is radial keratotomy, in which a surgeon makes 8-16 slices in the cornea that radiate outwardly from the pupil like spokes of a wheel. These cuts weaken the cornea so its edges bulge and the center flattens to refocus the light. The surgery takes about 15 minutes, can be done in a surgeon's office, and requires only a few days for the eye to recover. While this surgical technique is relatively safe in the short term, there are many drawbacks such as undercorrected vision, overcorrected vision, development of astigmatisms, glare from the surgical scars, and continued changing vision. Also, radial keratotomy is not reversible.

A second technique is to freeze a piece of cadaver cornea and grind it on a lathe to a predetermined corrective power. Once the tissue has been shaped, it is thawed and sewn onto the eye. If the newly-sewn cornea fails to correct the problem, the surgeon removes it and replaces it with another one.

However, there are problems with this technique. Grinding the frozen corneas into a contact lens is extremely difficult, and at the moment, there is only one institution which has the facilities to do it.

A third surgical approach, called keratophakia, sandwiches a thin layer of soft, pliable, transparent plastic into the middle of the cornea like icing between two halves of a cookie. The inserted material changes the shape of the cornea to refocus the light and correct vision.

The implanted material, called a hydrogel, consists of the same chemicals found in extended-wear contact lenses. And like contacts, hydrogels should give predictable correction because they can be precisely ground on a machine.

Keratophakia is also not without technical drawbacks. Not only is splitting the cornea in half a difficult procedure, after this, the surgeon must evenly insert the hydrogel, and then sew down the flap of the cornea. Since the tolerances are to fractions of a millimeter of curvature, it is easy to be off.

A fourth approach has been reported wherein a continuous plastic lens is placed on top of a recipient's cornea and held in place by donor corneal tissue. This approach, however has been unsuccessful because the donor cornea becomes necrotic, i.e., dies, due to a lack of a supply of nutrients from the recipient's eye.

Thus, there is a continuing need for a safe, reversible, and simple surgical treatment for refractive errors of the eye.

SUMMARY OF THE INVENTION

Accordingly, a primary object of the invention is to provide a surgical procedure for permanently correcting refractive errors in the human eye.

Another object of the invention is to provide an optical element, which when placed against a recipient's cornea and maintained in place by a donor cornea, will permanently aid in the correction of refractive errors, and also allow sufficient diffusion of nutrients from the recipient's cornea to the donor cornea.

The foregoing objects are basically attended by an optical element which is designed to be placed onto a recipient's cornea, and which has at least one opening therein for the diffusion of nutrients from the cornea. The element is held in place by an optical covering, such as a donor cornea, which is placed over the element and attached to the recipient's cornea.

Other objects, advantages and salient features of the present invention will become apparent from the following detailed description, which, taken in conjunction with the annexed drawings, discloses a preferred embodiment of the invention.

DRAWINGS

Referring now to the drawings which form a part of this original disclosure:

FIG. 4 is a top plan view of a first modified optical element in accordance with the present invention;

FIG. 5 is a side elevational view in longitudinal section of the optical element of FIG. 4 taken along line 5—5 in FIG. 4;

FIG. 6 is a top plan view of a second modified optical element in accordance with the invention;

FIG. 7 is a side elevational view in longitudinal section of the optical element of FIG. 6 taken along line 7—7 in FIG. 6;

FIG. 8 is a top plan view of a third modified optical element in accordance with the invention;

FIG. 9 is a side elevational view in longitudinal section of the element of FIG. 8 taken along line 9—9 in FIG. 8;

FIG. 10 is a top plan view of a fourth modified optical element in accordance with the invention;

FIG. 11 is a side elevational view in longitudinal section of the optical element of FIG. 10 taken along line 11—11 in FIG. 10;

FIG. 12 is a top plan view of a fifth modified optical element in accordance with the invention; and FIG. 13 is a side elevational view in longitudinal section of the optical element of FIG. 12 taken along line 13—13 in FIG. 12.

DETAILED DESCRIPTION OF THE INVENTION

Figure 1:
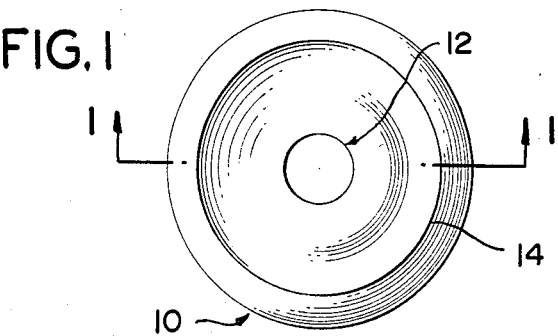
FIG. 1 is a top plan view of an optical element in accordance with the present invention.
Figure 2:
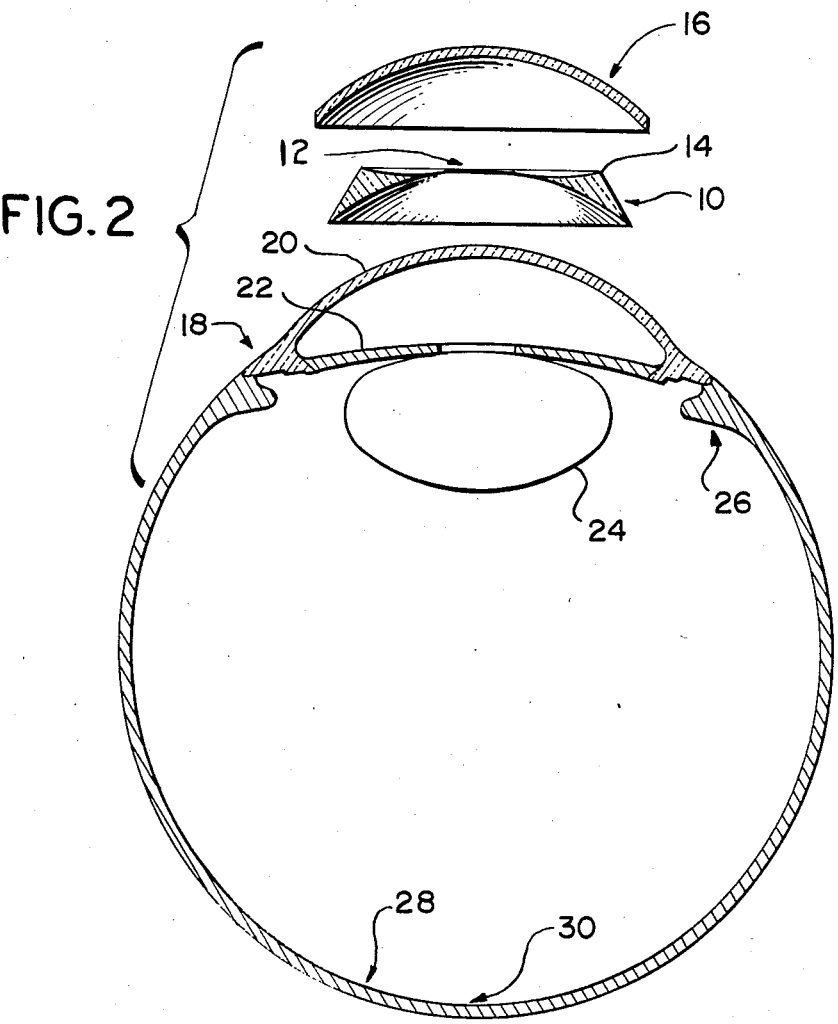
FIG. 2 is an exploded side elevational view in longitudinal section showing the positional relationship between the optical element of FIG. 1 which has been rotated 90° about the line 1—1, an optical covering, and an eye in accordance with the invention.
Figure 3:
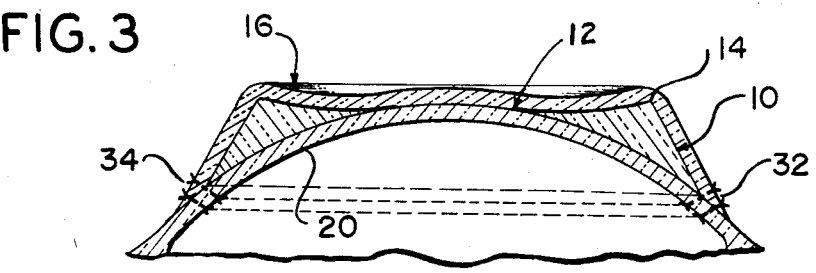
FIG. 3 is a side elevational view in longitudinal section in which the optical element of FIG. 1 has been placed onto the recipient's cornea, and covered with an optical covering which has been sutured to the recipient's cornea in accordance with the invention.

As seen in FIGS. 1, 2, and 3, an optical element 10 is shown having an opening 12 and a mid-peripheral portion 14.

As illustrated in FIGS. 2 and 3, optical element 10 is sandwiched between optical covering 16 and cornea 20. The eye 18 is shown including the cornea 20, the iris 22, lens 24, the ciliary sulcus 26 adjacent the lens, the retina 28 and the macula 30.

As illustrated in FIG. 3, the optical covering 16 is attached to the cornea 20 by sutures 32 nd 34, thereby holding optical element 10 in place over the cornea. Additional sutures, not shown, can also be used.

The optical element 10 has a substantially planar outer surface, a substantially frustoconical peripheral surface and an inner surface that is formed substantially as a portion of a sphere. The opening 12 extends from the inner surface, or first side, to the outer surface, or second side. In top and bottom plan view, the optical element is disk-shaped.

The optical element 10 is transparent and comprised of either a lens material, i.e., a material which will refract light, or an optically clear material which will not refract light. The optical element 10 can be ground or molded from suitable optical material such as optical glass, or polymeric material, which may be, for example, a hydrophillic polymer such as a hydrogel. Alternatively, it is contemplated that the element could be formed from an inherently porous synthetic or natural material such as, for example, a zeolitic compound.

If the element is a lens, it can be a collecting or positive lens, which is used in the correction of hyperopia, or it can be a diverging or negative lens which is used in the treatment of myopia, or it can be a lens specially ground to correct an astigmatism.

As shown in FIGS. 1-3, the lens 10 contains a through-opening or passageway 12 positioned approximately at the center of the lens. The opening 12 is provided to allow sufficient diffusion of nutrients to the donor cornea 16 from the recipient's cornea 20. Without the opening, insufficient diffusion of nutrients would occur resulting in necrosis of the donor corneal tissue.

The outside diameter of the element is from 2–10 millimeters, and the diameter of the single opening 12 can range from 0.24–8 millimeters.

Alternatively, as seen in FIGS. 6, 7, 10, 11, 12, and 13, the element may have more than one opening, each opening being of a different size and shape. Referring now to FIGS. 4 and 5, an element 36 is shown having opening 38, and mid-peripheral portion 40. FIGS. 4 and 5 illustrate an element which has a diverging or negative configuration and an opening 38 greater than opening 12 as seen in FIGS. 1-3.

FIGS. 6 and 7 also illustrate an element 42 having a diverging or negative configuration with a central outer surface that is concave. Element 42 has a circular opening 44 positioned approximately at the center of element 42, mid-peripheral portion 43, and a plurality of other openings, some of which are circular, such as 46, 47, and 48, and some of which are polygonal, such as 50, 52, and 54. The openings in element 42 are randomly positioned about center opening 44.

FIGS. 8 and 9 illustrate an element 56 having a single substantially frustoconical opening 58 therein positioned approximately at the center of the element 56, and mid-peripheral portion 60 formed substantially as a portion of a sphere interrupted by the opening 58. The shape of the optical elements in FIGS. 8-13 are that of a collecting or positive lens which would be used in the treatment of hyperopia.

It should again be noted that the optical element need not be a lens, but merely an optically clear element having the shape of a lens.

As seen in FIGS. 10 and 11, an optical element 62 in accordance with this invention is similar to element 56 in FIGS. 8 and 9, but contains a single opening 64 positioned approximately at the center of the element 62, and smaller cylindrical openings 66 positioned outside of the mid-peripheral portion 68 and approximately concentrically about the center opening 64.

As seen in FIGS. 12 and 13, an optical element 70 is shown having randomly spaced circular openings of varying diameters as illustrated by cylindrical openings 72, 74, and 76, as well as openings 78, 80, and 82, which are located in the edge of the optical element 70 and are in the form of slots.

Thus, as illustrated by FIGS. 4-13, the openings in the optical elements can be of any size, number, shape, and location on the element as desired or required.

As seen in FIGS. 2 and 3, an optical covering 16 of preferably uniform thickness is placed over the element 14 and attached to the recipient's cornea 20 via sutures, thereby retaining the optical element 14 in position over the cornea.

The optical covering can be comprised of any deformable, optically clear and transparent material, and is preferably a donor cornea.

The size of the optical covering 16 is a function of the size of optical element 14, i.e., the optical covering 16 must be large enough so that when placed over optical element 14, it has a sufficient overlap such that it may be surgically attached to the recipient's cornea 20.

The purpose of the optical element 14 and optical covering 16 are to correct refractive errors of the eye. It is easy to understand how refractive errors can be corrected if optical element 14 is a lens. However, as previously stated, optical element 14 need only be an optically clear material. This is because deformation of optical covering 16 will, in itself, provide refraction, as illustrated by the surgical procedure of radial keratotomy. The optical element need only be a means for deforming the optical covering in order to provide corrective refraction. Thus, it is the combination of the optical element and the optical covering which aid in correcting refractive errors, and not merely the element alone.

Besides the refractive properties discussed above, the optical covering also serves at least two other important functions. First, the optical covering securely holds the optical element in place over the recipient's cornea. Second, because the optical element has openings therein as illustrated in each of the figures, the optical covering serves to retain fluids in the openings themselves. The fluids, which are naturally produced by the eye, comprise essentially glucose and other metabolites having approximately the same refractive index as the element itself. This means that the combination of the optical element and the optical covering will provide a uniform correction, regardless of the fact that there are openings in the element itself. If an optical element such as a lens having openings therein were used without the optical covering, uneven refraction would occur, and the element would be essentially useless.

The method of correcting refractive errors of the eye using an optical element and optical covering simple and straightforward.

First, an opening must be provided in the element unless it is inherently porous as previously mentioned. The opening(s) can be made by laser, mechanical punch, or other suitable means capable of providing openings having dimensions ranging from about 1 micron up to several millimeters.

Then, the optical element is positioned onto the recipient's cornea, and the optical covering is placed over the optical element and attached to the recipient's cornea by any suitable means. Suitable means would include any means which could attach the optical covering to the recipient's cornea. For example, the optical covering could be sutured to the recipient's cornea for a period of time sufficient to allow the optical covering to permanently attached to the recipient's cornea via tissue growth. If a donor cornea is used as the optical covering, a period of 4—6 weeks will be requried before the sutures can be removed.

This invention also contemplates a pre-formed or pre-assembled combination of the optical element and optical covering such that the combination can be merely attached in one step to the recipient's cornea.

While several advantageous embodiments have been chosen to illustrate the invention, it will be understood by those skilled in the art that various changes and modifications can be made therein without departing from the scope of the invention as defined in the appended claims.

What is claimed is:

1. An optical assembly to be placed over a recipient's cornea for aid in correcting refractive errors of the eye, the combination comprising:
    a separate, deformable, and transparent optical covering adapted to be coupled to the recipient's cornea; and
    an optical element adapted to be located between said optical covering and the outer surface of the recipient's cornea, said element being a solid, having at least one opening therein for the diffusion of nutrients from the recipient's cornea and for directly engaging the outer surface of the recipient's cornea.

2. The device of claim 1, wherein
said at least one opening is positioned approximately at the center of said element.

3. The device of claim 2, and further comprising.
a plurality of additional openings in said optical element.

4. The device of claim 3, wherein
said plurality of additional openings are positioned approximately concentrically around said one opening.

5. The device of claim 1, and further comprising
a plurality of openings in said optical element.

6. The device of claim 1, wherein
said optical element comprises a lens.

7. The device of claim 6, wherein
said lens is a positive lens.

8. The device of claim 6, wherein
said lens is a negative lens.

9. The device of claim 6, wherein
said lens comprises a polymeric material.

10. The device of claim 9, wherein
said polymeric material comprises a hydrophillic polymer.

11. The device of claim 1, wherein
said element comprises an optically clear material.

12. The device of claim 11, wherein
said element comprises a polymeric material.

13. The device of claim 12, wherein
said polymeric material comprises a hydrophillic polymer.

14. The optical assembly of claim 1, wherein
said optical covering comprises a donor cornea, and said optical element comprises a lens.

15. The optical assembly of claim 14, wherein
said opening is positioned approximately at the center of said element.

16. The optical assembly of claim 14, wherein
said opening is positioned approximately at the center of said element.

17. A method for at least partially correcting refractive errors of the eye, comprising the steps of
    positioning onto the outer surface of a recipient's cornea an optical assembly comprising an optical element having at least one opening therein for the diffusion of nutrients from the recipient's cornea, and a separate, deformable, and transparent optical covering overlying the optical element, the optical element directly engaging the outer surface of the recipient's cornea and being a solid, and
    securing the optical covering to the recipient's cornea.

18. The method of claim 17, wherein the step of positioning comprises.
    positioning the optical element onto the recipient's cornea, and
    placing the optical covering over the element.

19. The method of claim 17 wherein the step of securing comprises
    suturing the optical assembly to the recipient's cornea, such that the covering and element are securely held in place over recipient's cornea.

* * * * *